United States Patent
Dalbert

(10) Patent No.: US 11,786,431 B2
(45) Date of Patent: Oct. 17, 2023

(54) STABILIZATION DEVICE

(71) Applicant: TRUMPF MEDIZIN SYSTEME GMBH + CO. KG, Saalfeld (DE)

(72) Inventor: Heinz-Hermann Dalbert, Uhlstadt-Kirchhasel (DE)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 1146 days.

(21) Appl. No.: 16/456,682

(22) Filed: Jun. 28, 2019

(65) Prior Publication Data

US 2020/0008997 A1 Jan. 9, 2020

(30) Foreign Application Priority Data

Jul. 3, 2018 (EP) .................................... 18181529

(51) Int. Cl.
*A61G 13/10* (2006.01)
*A61B 34/30* (2016.01)
*B25J 9/00* (2006.01)

(52) U.S. Cl.
CPC ............ *A61G 13/101* (2013.01); *A61B 34/30* (2016.02); *B25J 9/0009* (2013.01)

(58) Field of Classification Search
CPC ............................. A61G 13/101; A61B 34/30; A61B 2090/571; B25J 9/0009; B25J 9/009
USPC ....................................................... 248/592
See application file for complete search history.

(56) References Cited

U.S. PATENT DOCUMENTS

| | | | | |
|---|---|---|---|---|
| 4,143,652 A | * | 3/1979 | Meier | F16M 13/022 600/230 |
| 5,287,575 A | * | 2/1994 | Allen | A61G 13/101 5/507.1 |
| 8,621,692 B1 | * | 1/2014 | Kring | A61G 13/101 5/503.1 |
| 11,013,574 B1 | * | 5/2021 | Gomez | A61B 17/00234 |
| 2005/0080321 A1 | * | 4/2005 | Bjork | A61B 1/32 600/230 |
| 2005/0223494 A1 | * | 10/2005 | Ambrose, III | A61G 13/101 5/658 |
| 2010/0152749 A1 | | 6/2010 | Von Pechmann et al. | |
| 2014/0316436 A1 | * | 10/2014 | Bar | A61B 34/32 901/9 |
| 2018/0078440 A1 | | 3/2018 | Shakespear et al. | |
| 2018/0133006 A1 | * | 5/2018 | Jones | A61F 2/24 |

(Continued)

FOREIGN PATENT DOCUMENTS

CN 103027818 A 4/2013
WO WO2018/053282 3/2018

*Primary Examiner* — Myles A Throop
(74) *Attorney, Agent, or Firm* — Barnes & Thornburg LLP

(57) ABSTRACT

A stabilization device for stabilizing a robotic arm is provided attached at a fixing point on a predefined side of an operating table is provided. The stabilization device comprises a first fixation device configured to attach the stabilization device to the robotic arm, a support structure joined to the first fixation device, and a second fixation device joined to the support structure, the second fixation device being configured to fix the stabilization device to the operating table. The first fixation device is attachable to the robotic arm, and the stabilization device is configured such that the second fixation device is fixable to the operating table at a fixation location located at another place than at the predefined side of the operating table.

15 Claims, 2 Drawing Sheets

(56) References Cited

U.S. PATENT DOCUMENTS

| | | | |
|---|---|---|---|
| 2018/0140364 A1* | 5/2018 | Schena | A61B 17/00234 |
| 2020/0108225 A1* | 4/2020 | Jamal | A61F 2/2427 |
| 2021/0137635 A1* | 5/2021 | Gomez | B25J 5/02 |
| 2021/0236207 A1* | 8/2021 | Stanton | A61B 34/74 |

* cited by examiner

STABILIZATION DEVICE

CROSS-REFERENCE TO RELATED APPLICATIONS

This application claims the benefit of European Patent Application Serial No. 18181529.1, filed on Jul. 3, 2018, the entire disclosure of which is incorporated herein by reference in its entirety.

BACKGROUND

The present disclosure relates to a stabilization device, in particular to a stabilization device for stabilizing a robotic arm attached to an operating table.

Robotic arms for performing surgeries spread in the recent past. One advantage for using the robotic arms for the surgeries are that the surgeon can take an attitude which is comfortable also during a long-term surgery. Another advantage is that the surgeon is not necessarily present in the operating theater but can be in another room of the hospital or in another hospital, even in another city or country.

However, in particular during surgeries at nerves and blood vessels, a very exact positioning of the surgical tools during the intervention is necessary. This can be done by attaching the robotic arm to an operating table and exactly fixing the patient on the operating table. However, attachable robotic arms are quite new on the market and there is no existing solution available to ensure a proper and backlash-free attachment.

Therefore, the object underlying the invention is to provide a stabilization device and a method for stabilizing for a robotic arm attachable to an operating table in an easy and economic manner. The object is achieved by a stabilization device, a system, and a method as disclosed below.

SUMMARY

According to an aspect of the present disclosure, a stabilization device for stabilizing a robotic arm attached at a predefined side of an operating table comprises a first fixation device configured to attach the stabilization device to the robotic arm, a support structure joined to the first fixation device, and a second fixation device joined to the support structure configured to fix the stabilization device to the operating table.

The first fixation device is attached to the robotic arm at a location and the stabilization device is configured such that the second fixation device is fixable to the operating table at a fixation location located at another place than at the predefined side of the operating table.

By providing such a stabilization device, the stabilization device can be attached to the operating table such that a long lever arm for exerting a holding torque to a robotic arm is possible. Therefore, the robotic arm can be attached to the operating table in a proper and backlash-free attachment such that the robotic arm is attached to the operating table in an easy and economic manner.

In one implementation of the stabilization device, a support dimension of the stabilization device is configured such that the fixation location of the first fixation device is located at a side of the operating table opposite to the predefined side of the operating table.

By configuring such a support dimension, a maximum support dimension of the stabilization device and, therefore, providing a holding torque as large as possible without interference with the operating personnel and apparatuses beside the operating table is possible.

In another implementation of the stabilization device, the second fixation device is configured to be attached to a side rail of the operating table.

When being configured to be attached to the side rail of the operating table, no further fixation points at the operating table are necessary so that the stabilization device can be attached to the operating table in an economic and flexible manner.

In yet another implementation of the stabilization device, the first fixation device comprises a cone.

By using the second fixation device comprising the cone, a backlash-free between the stabilization device and the robotic arm can easily be ensured.

In still another implementation of the stabilization device, the support structure is substantially L-shaped having a long leg joined to the first fixation device and short leg joined to the second fixation device.

By the L-shape of the stabilization device, the robotic arm can be supported using large lever arms while using the standard side rail as an attachment device and considering components of the operating table below a table top.

In a yet still further implementation of the stabilization device, the long leg is bar-shaped.

By using the stabilization device having the bar-shaped long leg, little space demand for stabilizing the robotic arm is necessary so that, e.g., relating to the operating table, a use of a C-arm X-ray unit is not or merely little impaired.

In a further implementation of the stabilization device, the long leg is configured to be adjustable in length.

By such a configuration, the stabilization device can be adapted to various medical apparatuses having different dimensions.

In a another implementation of the stabilization device, the support structure comprises a threaded connection configured to adjust a length of the long leg.

Due to the threaded connection for adjusting the length, on the one hand, the length can be finely adjusted for exactly being adapted to a distance of the fixation points of the first and second fixation devices and, on the other hand, the stabilization device and, therefore, the robotic arm can be preloaded for avoiding micro movements of the robotic arm.

According to a further aspect of the disclosure, a system comprising the operating table, the robotic arm, and the stabilization device is provided.

This system enables safe robot-assisted surgeries on a patient positioned on the operating table.

In an implementation of the system, the first fixation device joined to the support structure is attached to the robotic arm, and the second fixation device is fixed to the operating table at the fixation location located at another place than at the predefined side of the operating table.

By providing such a system, the robotic arm can be attached to the operating table in a proper and backlash-free attachment such that the robotic arm is attached to the operating table in an easy and economic manner.

According to still another aspect of the disclosure, a method for stabilizing a robotic arm attached to a predefined side of an operating table comprises the steps: attaching the first fixation device of the stabilization device to the robotic arm and fixing the second fixation device to the operating table at a fixation location located at another place than the predefined side of the operating table.

By performing this method, the stabilization device can be attached to the operating table such that a long lever arm for exerting a holding torque to a robotic arm is possible.

Therefore, the robotic arm can be attached to the operating table in a proper and backlash-free attachment such that the robotic arm is attached to the operating table in an easy and economic manner.

In an implementation of the method, the second fixation device is fixed to the operating table by clamping the second fixation device to the side rail.

Clamping the second fixation device to the side rail of the operating table enables an easy and quick fixation of the stabilization device to the operating table.

In one implementation of the method, the first fixation device is fixed to the robotic arm by tightening a cone by a bolt.

Due to the fixation of the stabilization device by the first fixation device by means of tightening the cone to the robotic arm by the bolt, an easy and backlash-free connection between the robotic arm and the stabilization device is enabled such that micro movements of the robotic arm can easily be avoided.

In one implementation of the method, the length of the long leg of the stabilization device is adjusted by operating a threaded connection according to an actual distance between a fixation location of the second fixation device and an accommodation of the robotic arm for the first fixation device.

By adjusting the length of the long leg of the stabilization device, the stabilization device can easily be adjusted to various types of the operating table and the stabilization device can be preloaded in order to avoid micro movements of the robotic arm.

In one implementation of the method, the stabilization device fixed to the operating table and to the robotic arm is preloaded by adjusting a length of the long leg of the stabilization device by operating the threaded connection of the stabilization device.

By adjusting the length of the long leg of the stabilization device by operating the threaded connection of the stabilization device, the stabilization device can very easily preloaded.

BRIEF DESCRIPTION OF THE DRAWINGS

Now, the invention is elucidated by means of an embodiment referring to the attached drawings.

DETAILED DESCRIPTION OF THE DRAWINGS

Figure 1:
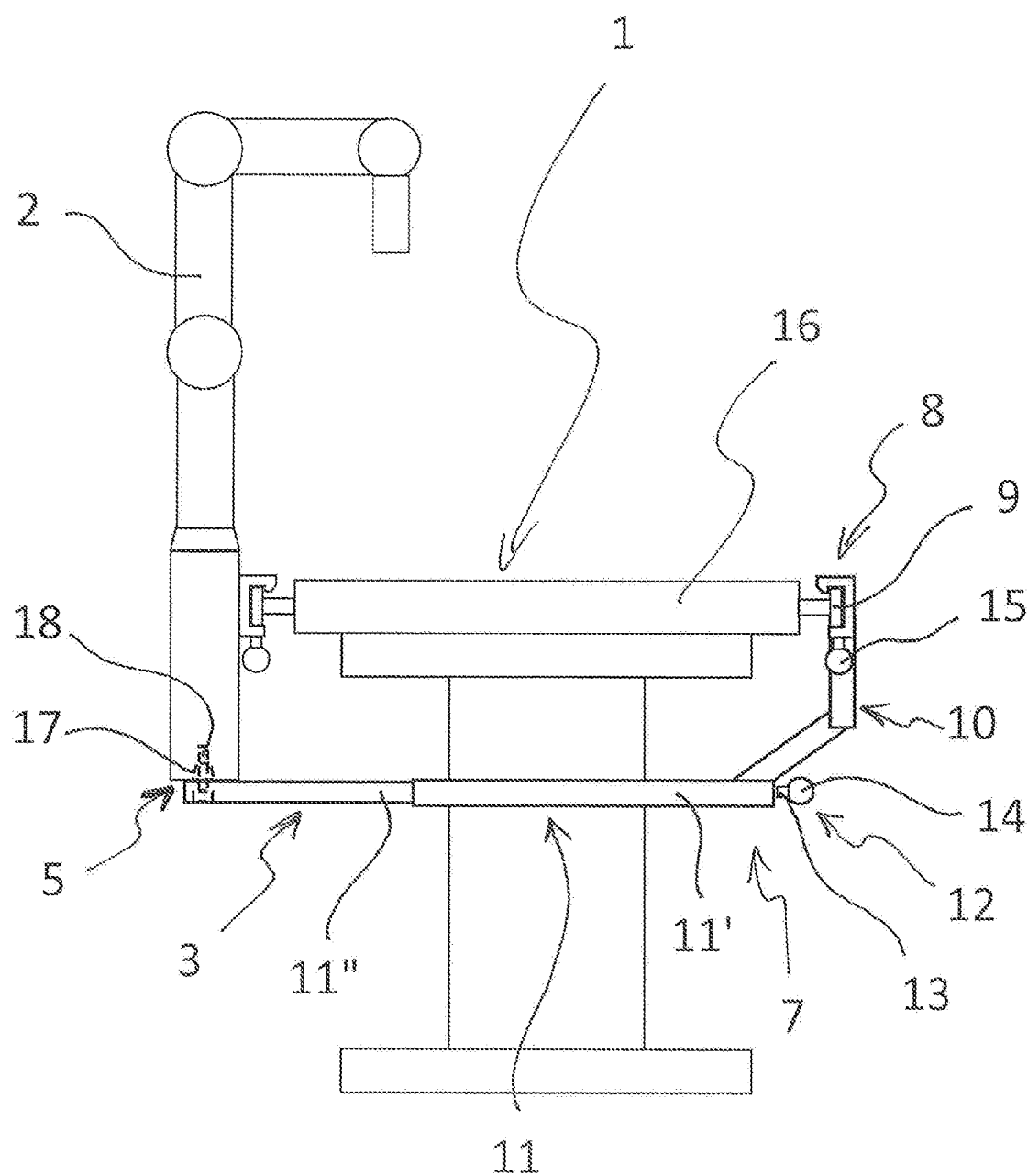
FIG. 1 shows a front view of an operating table provided with a robotic arm and a stabilization device according to the present disclosure.

FIG. 1 shows a front view of an operating table 1. The operating table 1 is provided with a robotic arm 2 and a stabilization device 3 for stabilizing the robotic arm 2 attached at a predefined side of the operating table 1.

The stabilization device 3 comprises a first fixation device 5 for attaching the stabilization device 3 to the robotic arm 2 and a second fixation device 8 for fixing the stabilization device 3 to the operating table 1 at a fixation location located at another place than at the predefined side of the operating table 1. Further, the stabilization device 3 comprises a support structure 7 joined to the first fixation device 5 and to the second fixation device 8. Alternatively, the stabilization device 3 comprises the first fixation device 5 for attaching the stabilization device 3 to the robotic arm 2 spaced from a fixing point of the robotic arm 2 to the operating table 1.

In this embodiment, an additional lever arm for supporting the robotic arm 2 can be provided.

A support dimension of the stabilization device 7, i.e., a distance between the first fixation device 5 and the second fixation device 8 in a horizontal direction in a mounted state, is configured such that the fixation location of the second fixation device 8 is located at a side of the operating table 1 opposite to the predefined side of the operating table 1. In an alternative embodiment, the fixation location is not located at the side of the operating table 1 opposite to the predefined side but it can also be located e.g. underneath a table top 16 as long as a lever arm, i.e., the support dimension of the stabilization device 7, is long enough for securely stabilizing the robotic arm 2.

The support structure 7 of the stabilization device 3 is substantially L-shaped having a short leg 10 joined to the second fixation device 8 and a long leg 11 joined to the first fixation device 5. In an alternative embodiment, the support structure 7 is not L-shaped but has another suitable shape for providing a sufficient lever arm for stabilizing the robotic arm 2 and for joining the first fixation device 5 and the second fixation device 8, e.g., it is Z-shaped.

The long leg 11 of the support structure 7 is bar-shaped. Alternatively, the support structure 7 is not bar-shaped but it has another suitable shape, e.g., it is plate-shaped. Furthermore, the long leg 11 comprises two parts 11', 11" which are configured to telescope such that the long leg 11 is configured to be adjustable in length. For adjusting the length of the long leg 11, the support structure 7 comprises a threaded connection 12. The threaded connection 12 comprises a threaded rod 13 and a handle 14. In alternative embodiments, the long leg 11 is not adjustable in length but, in particular, if the support structure 7 has another shape, another portion of the stabilization device 3 is adjustable such that the support dimension of the stabilization device 3 is adjustable. In a further alternative embodiment, the support dimension of the stabilization device 3 is not adjustable but it is fixedly predefined for a certain combination of the operating table 1 and the robotic arm 2.

The first fixation device 5 comprises a cone 17 and a bolt 18 for tightening the cone 17 to the robotic arm 2. Alternatively, the first fixation device 5 is not provided with a cone 17 and/or a bolt 18 but it is fixed by another fixing equipment, e.g. by a fit bolt or another fixing equipment ensuring a backlash-free connection between the stabilization device 3 and the robotic arm 2.

The second fixation device 8 is attached to a side rail 9 of the operating table 1. For being attached to the side rail 9, the second fixation device 8 comprises a clamping device 15.

Figure 2:
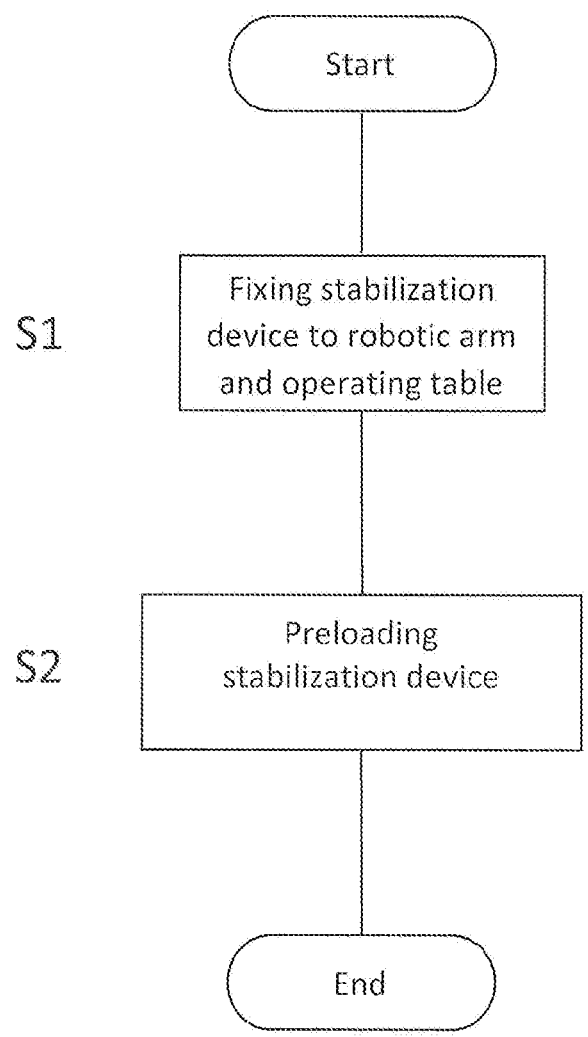
FIG. 2 shows a flowchart of a method according to the present disclosure.

FIG. 2 shows a flowchart of a method according to the present disclosure.

In use, in step S1, the stabilization device 3 is fixed to the robotic arm 2 and to the operating table 1.

The robotic arm 2 is stabilized by means of the stabilization device 3 by attaching the first fixation device 5 of the stabilization device 3 to the robotic arm 2 on the predefined side of the operating table 1 and by fixing the second fixation device 8 to the operating table 1 at the fixation location located at another place than at the predefined side of the operating table 1 where the robotic arm 2 is attached.

The first fixation device 5 of the stabilization device 3 is fixed to the robotic arm 2 by tightening the cone 17 by means of the bolt 18. Alternatively, the first fixation device 5 is fixed to the robotic arm 2 by another fixing method.

The second fixation device 8 of the stabilization device 3 is fixed to the operating table 1 by clamping the second fixation device 8 to the side rail 9. However, alternatively, another fixing method, e.g., screwing on the operating table 1, is possible.

The length of the long leg 11 of the stabilization device 3 is adjusted by operating the threaded connection 12 according to an actual distance between an accommodation of the robotic arm 2 for the first fixation device 5 and a fixation location of the second fixation device 8. Alternatively, the length of the long leg 11 is adjusted in another manner, another portion of the stabilization device 3 is adjusted to adjust the length of the stabilization device 3, or no length adjustment is performed.

In step S2, the stabilization device 3 fixed to the operating table 1 and attached to the robotic arm 2 is preloaded by adjusting the length of the long leg 11 of the stabilization device 3 by operating the threaded connection 12 of the stabilization device 3. The stabilization device 3 is preloaded by rotating the threaded connection 12 at a maximal torque of 1 Nm. Alternatively, no preloading is performed or the preloading is performed by preloading at another suitable torque or by adjusting another portion of the stabilization device 3.

While the invention has been illustrated and described in detail in the drawings and the foregoing description, such illustration and description are to be considered illustrative or exemplary and not restrictive. The invention is not limited to the disclosed embodiment. From reading the present disclosure, other modifications will be apparent to a person skilled in the art. Such modifications may involve other features, which are already known in the art and may be used instead of or in addition to features already described herein. In the claims, the word "comprising" does not exclude other elements or steps, and the indefinite article "a" or "an" does not exclude a plurality.

The invention claimed is:

1. A stabilization device for stabilizing a robotic arm attached at a fixing point on a predefined side of an operating table, the stabilization device comprising
a first fixation device configured to attach the stabilization device to the robotic arm at a location spaced away from the fixing point on the predefined side of the operating table,
a support structure joined to the first fixation device, and
a second fixation device joined to the support structure, the second fixation device being configured to fix the stabilization device to the operating table,
wherein the first fixation device is attachable to the robotic arm,
the stabilization device is configured such that the second fixation device is fixable to the operating table at a fixation location located at another place than at the predefined side of the operating table, and
the support structure has at least one leg having a variable length, the length of the at least one leg being adjustable to vary the preload in the at least one leg to a predefined load to prevent micro movements of the robotic arm.

2. The stabilization device of claim 1, wherein a support dimension of the stabilization device is configured such that the fixation location of the second fixation device is located at a side of the operating table opposite to the predefined side of the operating table.

3. The stabilization device of claim 2, wherein the second fixation device is configured to be attached to a side rail of the operating table.

4. The stabilization device of claim 3, wherein the first fixation device comprises a cone.

5. The stabilization device of claim 4, wherein the support structure is substantially L-shaped having a long leg joined to the first fixation device and a short leg joined to the second fixation device.

6. The stabilization device of claim 5, wherein the long leg is bar-shaped.

7. The stabilization device of claim 5, wherein the long leg is configured to be adjustable in length.

8. The stabilization device of claim 7, wherein the support structure comprises a threaded connection configured to adjust a length of the long leg.

9. The stabilization device of claim 5, wherein the long leg is plate-shaped.

10. The stabilization device of claim 4, wherein the first fixation device further comprises a bolt to tighten the cone.

11. The stabilization device of claim 4, wherein the support structure is adjustable.

12. The stabilization device of claim 1, wherein the second fixation device comprises a clamping device.

13. The stabilization device of claim 1, wherein the second fixation device is fixed to the operating table by a screw.

14. The stabilization device of claim 1, wherein the support structure is shaped for joining the first fixation device and the second fixation device.

15. The stabilization device of claim 1, wherein a support dimension of the stabilization device is configured such that the fixation location of the second fixation device is located underneath the operating table.

* * * * *